(12) United States Patent
Chu et al.

(10) Patent No.: US 6,210,416 B1
(45) Date of Patent: Apr. 3, 2001

(54) COAXIAL NEEDLE AND SEVERING SNARE

(76) Inventors: Michael S. H. Chu, 121 Browne St., Brookline, MA (US) 02146; Yem Chin, 35 University Ave., Burlington, MA (US) 01803

(*) Notice: Subject to any disclaimer, the term of this patent is extended or adjusted under 35 U.S.C. 154(b) by 0 days.

(21) Appl. No.: 09/357,105

(22) Filed: Jul. 19, 1999

Related U.S. Application Data

(62) Division of application No. 09/025,499, filed on Feb. 18, 1998, now Pat. No. 5,961,526.

(51) Int. Cl.[7] .................................................. A61B 17/24
(52) U.S. Cl. .............................................................. 606/113
(58) Field of Search .......................... 606/113, 79, 110, 606/148; 600/104, 156, 153

(56) References Cited

U.S. PATENT DOCUMENTS

| | | |
|---|---|---|
| 798,839 | 9/1905 | Stowe . |
| 1,606,497 | 11/1926 | Berger . |
| 2,737,181 | 3/1956 | Beard . |
| 3,155,094 | 11/1964 | Hamilton . |
| 3,382,273 | 5/1968 | Banich et al. . |
| 3,687,138 | 8/1972 | Jarvik . |
| 3,760,810 | 9/1973 | Van Hoorn . |
| 3,834,392 | 9/1974 | Lampman et al. . |
| 3,870,048 | 3/1975 | Yoon . |
| 3,911,923 | 10/1975 | Yoon . |
| 3,934,589 | 1/1976 | Zimmer . |
| 3,958,576 | 5/1976 | Komiya . |
| 3,967,625 | 7/1976 | Yoon . |
| 3,989,049 | 11/1976 | Yoon . |
| 4,085,743 | 4/1978 | Yoon . |
| 4,103,680 | 8/1978 | Yoon . |
| 4,222,380 | 9/1980 | Terayama . |
| 4,226,239 | 10/1980 | Polk et al. . |
| 4,230,116 | 10/1980 | Watson . |
| 4,257,419 | 3/1981 | Goltner et al. . |
| 4,257,420 | 3/1981 | Terayama . |
| 4,267,839 | 5/1981 | Laufe et al. . |
| 4,374,523 | 2/1983 | Yoon . |
| 4,471,766 | 9/1984 | Terayama . |
| 4,548,201 | 10/1985 | Yoon . |
| 4,735,194 | 4/1988 | Stiegmann . |
| 4,794,927 | 1/1989 | Yoon . |
| 4,990,152 | 2/1991 | Yoon . |
| 5,026,379 | 6/1991 | Yoon . |
| 5,122,149 | 6/1992 | Broome . |
| 5,171,314 | 12/1992 | Dulebohn . |
| 5,203,863 | 4/1993 | Bidoia . |

(List continued on next page.)

OTHER PUBLICATIONS

Ayao Torii, et al., Endoscopic Aspiration Mucosectomy as Curative Endoscopic Surgery, Gastrointestinal Endoscopy, vol. 42, No. 5, Nov. 1995, pp. 475–479.

*Primary Examiner*—Todd E. Manahan
*Assistant Examiner*—Eduardo C. Robert
(74) *Attorney, Agent, or Firm*—Kenyon & Kenyon

(57) ABSTRACT

A device for treating a lesion comprises a sheath extending from a proximal end which, in an operative position, is located outside the body, to a distal end which, in the operative position is located within the body. A needle extending through the sheath has a tissue piercing distal tip and a central lumen extending through the needle from a proximal port to a distal opening formed in the distal tip and a needle actuator is provided for moving the needle between a retracted position in which the distal tip is received within the sheath to an injection position in which the distal tip extends distally beyond a distal end of the sheath. A snare extends within the lumen to a loop formed in a distal end of the snare and a snare actuator is provided for moving the snare between a covered position in which the loop is received within the lumen and an extended position in which the loop extends distally from the lumen beyond the distal tip.

14 Claims, 12 Drawing Sheets

U.S. PATENT DOCUMENTS

| | | |
|---|---|---|
| 5,236,434 | 8/1993 | Callicrate . |
| 5,243,976 | 9/1993 | Ferek-Petric et al. . |
| 5,269,789 | 12/1993 | Chin et al. . |
| 5,300,078 | 4/1994 | Buelna . |
| 5,320,630 | 6/1994 | Ahmed . |
| 5,336,227 | 8/1994 | Nakao et al. . |
| 5,376,094 | 12/1994 | Kline . |
| 5,417,697 | 5/1995 | Wilk et al. . |
| 5,419,309 * | 5/1995 | Biehl .................................... 600/156 |
| 5,423,834 | 6/1995 | Ahmed . |
| 5,425,736 | 6/1995 | Wadsworth . |
| 5,462,559 | 10/1995 | Ahmed . |
| 5,507,797 | 4/1996 | Suzuki et al. . |
| 5,542,948 | 8/1996 | Weaver et al. . |
| 5,569,268 | 10/1996 | Hosoda . |
| 5,697,940 | 12/1997 | Chu et al. . |
| 5,752,961 | 5/1998 | Hill . |
| 5,814,052 | 9/1998 | Nakao et al. . |

\* cited by examiner

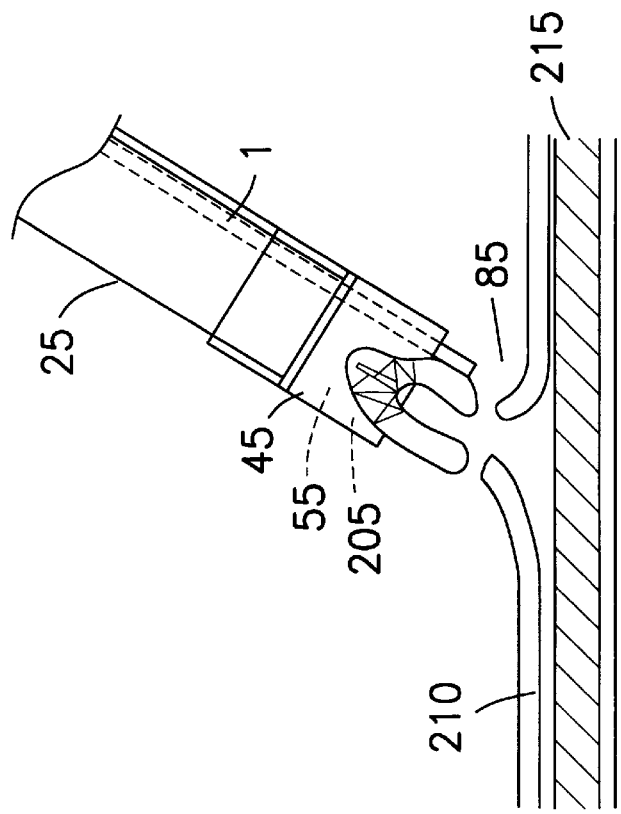
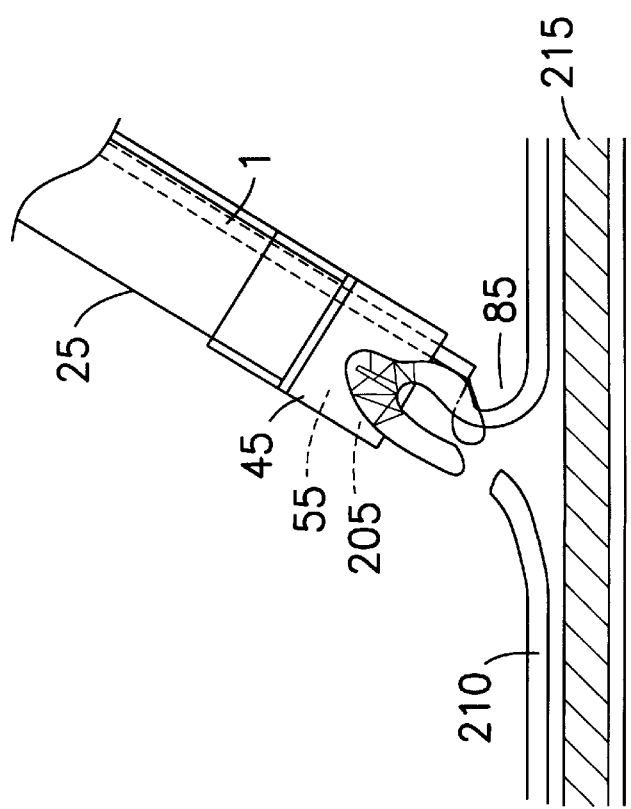

COAXIAL NEEDLE AND SEVERING SNARE

This is a division of application Ser. No. 09/025,499, filed Feb. 18, 1998, U.S. Pat. No. 5,961,526.

FIELD OF THE INVENTION

The present invention relates generally to the field of tissue ligation, and more particularly to an improved device and method for severing lesions.

BACKGROUND OF THE INVENTION

A wide variety of lesions, including internal hemorrhoids, polyps, and mucositis, may be treated by severing snare ligation.

In severing snare ligation, a targeted lesion is removed from the surrounding tissue by an electrosurgical severing snare using radio frequency (R/F) electric current to sever tissue or to achieve hemostasis. A high radio frequency is used (i.e., above 100,000 Hz.) to avoid the potentially injurious stimulation of muscles and nerves which results from lower frequency R/F energy. Thus, electrosurgery is typically performed at frequencies of approximately 500,000 Hz., although frequencies as high as 4,000,000 Hz. may be used.

Medical diathermy is similar to electrosurgery in that radio frequency current is passed through the patient's body. The major difference between these two techniques is the density of the radio frequency electric current; the current density used in medical diathermy is kept low to reduce tissue heating and to prevent necrosis.

There are three surgical effects that can be achieved with electrosurgery. These include electrosurgical desiccation, which is a low power coagulation caused without sparking to the tissue; electrosurgical cutting, where electricity sparks to the targeted tissue and produces a cutting effect; and electrosurgical fulguration, where electricity sparks to the targeted tissue without causing significant cutting.

The above-described surgical effects can be accomplished by using either a monopolar or bipolar output. For many applications, however, bipolar outputs are preferable because the patient return electrode (necessary in monopolar procedures and a common source of accidents) is eliminated, and any desiccation performed is extremely localized because, in a true bipolar operation, only the tissue that is grasped between the two electrodes is desiccated. Bipolar output, however, is less effective for cutting and fulgurating, and thus monopolar tools remain commonplace. Severing snares, for example, are almost all monopolar instruments.

In addition, three types of electrical current waveforms are typically used in electrosurgery. These include a "cutting" waveform, which cuts tissue very cleanly but may cause the incised tissue to bleed excessively; a "coagulating" waveform, which desiccates and fulgurates tissue without significant cutting; and a "blended" waveform, which is a cutting waveform that has a moderate hemostatic effect. A waveform's "Crest Factor" describes the degree of hemostasis that a waveform will produce if properly applied.

To remove a lesion (or polyp) with an electrosurgical severing snare, the wire snare is looped around the targeted lesion and is tightened as the snare is drawn into the sheath. The lesion is then desiccated and cut through electrosurgically. It is also possible to sever a lesion in a single step by cutting with a "blended" current. This allows a snare to cut through a lesion in one pass without having to worry about bleeding. Alternately, the lesion may be cut through mechanically with a thin snare wire after the blood supply to the targeted tissue has been coagulated and the tissue has been softened by a desiccation current.

Saline-Assisted Polypectomy (SAP), or "strip biopsy," has become an increasingly popular way of performing endoscopic mucosal resection (EMR) to diagnose and treat diseases of the gastrointestinal tract. When performing SAP, a surgeon passes a needle through an endoscope and inserts the needle into the submucosa layer proximate to the lesion. Next, the surgeon injects physiological saline into the submucosa to elevate the lesion on a bed of saline solution. Once elevated, the surgeon can easily remove the lesion by passing an electrosurgical severing snare over the lesion and ligating the lesion. SAP, however, typically requires the use of a large diameter double-channel endoscope, which is difficult to introduce into the patient and is hard to manipulate. In addition, grasping forceps must be used to lift the lesion off of the layer of saline solution, which may result in a tear in the mucosa.

Accordingly, an alternate procedure has been developed called endoscopic aspiration mucosectomy (EAM). As described by Torii et al. in "Endoscopic Aspiration Mucosectomy as Curative Endoscopic Surgery," *Gastrointestinal Endoscopy*, Vol. 42, No. 5 (1995), EAM can be used to lift up a targeted lesion with suction, rather than with forceps, thereby reducing the risk of injury to the mucosal surface. When performing EAM, a double-channel endoscope is introduced into the patient, the lesion is marked with a needle knife, and saline solution or Glyceol™ (e.g., a hypertonic solution of 10% glycerol, 5% fructose, and physiological saline solution; available from Chugai Pharmaceutical Co., Tokyo, Japan) is injected into the submucosal layer beneath the lesion to separate the lesion from the layer. Next, the double-channel endoscope is withdrawn from the patient and a single-channel, video endoscope equipped with a transparent aspiration cylinder is introduced into the patient and (e.g., a Teflon® tube through which suction is applied) an electrosurgical severing snare is tightened around the outer circumference of the cylinder.

Once the single-channel endoscope has been properly repositioned near the targeted lesion, the lesion and the surrounding mucosa are aspirated into the cylinder and the snare is pushed off the cylinder and tightened around the lesion to ligate the lesion. By first aspirating the lesion into the tube before severing it, the lesion may be severed further down on the stalk than possible with SAP. After the targeted lesion has been severed from the surrounding tissue, the severed tissue may remain aspirated into the cylinder to retrieve the sample for further study. Alternately, the severed tissue may be aspirated out of the cylinder to pass through the body naturally.

However, while the EAM procedure described by Torii et al. may offer certain advantages over SAP, it still has its disadvantages. To perform EAM, a surgeon must switch between a double-channel endoscope having a needle knife and an injection needle (for marking the lesion and injecting solution), and a more maneuverable single-channel endoscope having a severing snare and an aspiration cylinder (for ligating and aspirating the lesion) because the working channel of a single-channel endoscope cannot accommodate both an injection needle and a severing snare simultaneously. Alternately, as discussed by Torii et al., double-channel endoscopes are too large and are not desirable for the EAM procedure. Exchanging endoscopes, however, is time consuming-wasting surgeons' time and prolonging the procedure.

U.S. Pat. No. 5,542,948 to Weaver et al. purports to disclose an instrument in which a severing snare and an injection needle disposed side-by-side in separate lumens of the device are prevented from being simultaneously deployed by an actuator assembly which maintains one of the instruments (e.g., the severing snare) within the lumen until the other instrument (e.g., the injection needle) has been completely withdrawn into its respective lumen.

This requires the use of a multi-lumen sheath including two lumens for carrying the injection needle and severing snare. However, multi-lumen sheaths take up valuable space and make the overall endoscopic apparatus large and bulky. The use of two lumens within a sheath also limits the size of the severing snare and injection needle that can be used, as the instruments are disposed through the sheath side-by-side.

In addition, the depth at which a surgeon using the apparatus disclosed by Weaver et al. may sever a lesion is limited because the device is designed to be used when performing SAP and does not, therefore, provide for an aspirating device. This prevents the use of the device of Weaver et al. in performing EAM.

SUMMARY OF THE INVENTION

The present invention is directed to a device for treating a lesion within a living body, comprising a sheath extending from a proximal end which, in an operative position, is located outside the body, to a distal end which, in the operative position is located within the body. A needle extending through the sheath defines a tissue piercing distal tip and a central lumen extends through the needle from a proximal port to a distal opening formed in the distal tip. A needle actuator is provided for moving the needle between a retracted position in which the distal tip is received within the sheath to an injection position in which the distal tip extends distally beyond a distal end of the sheath and a snare extends within the lumen to a loop formed in a distal end of the snare. A snare actuator is provided for moving the snare between a covered position in which the loop is received within the lumen and an extended position in which the loop extends distally from the lumen beyond the distal tip.

BRIEF DESCRIPTION OF THE DRAWINGS

The invention will be more readily understood through the following detailed description, with reference to the accompanying drawings, in which:

FIG. 12 shows the apparatus according to the first embodiment with the targeted lesion being ligating by the severing snare;

FIG. 13 shows the apparatus according to the first embodiment with the now-severed lesion aspirated into the aspiration cylinder;

DETAILED DESCRIPTION

Figures 1A, 1B:
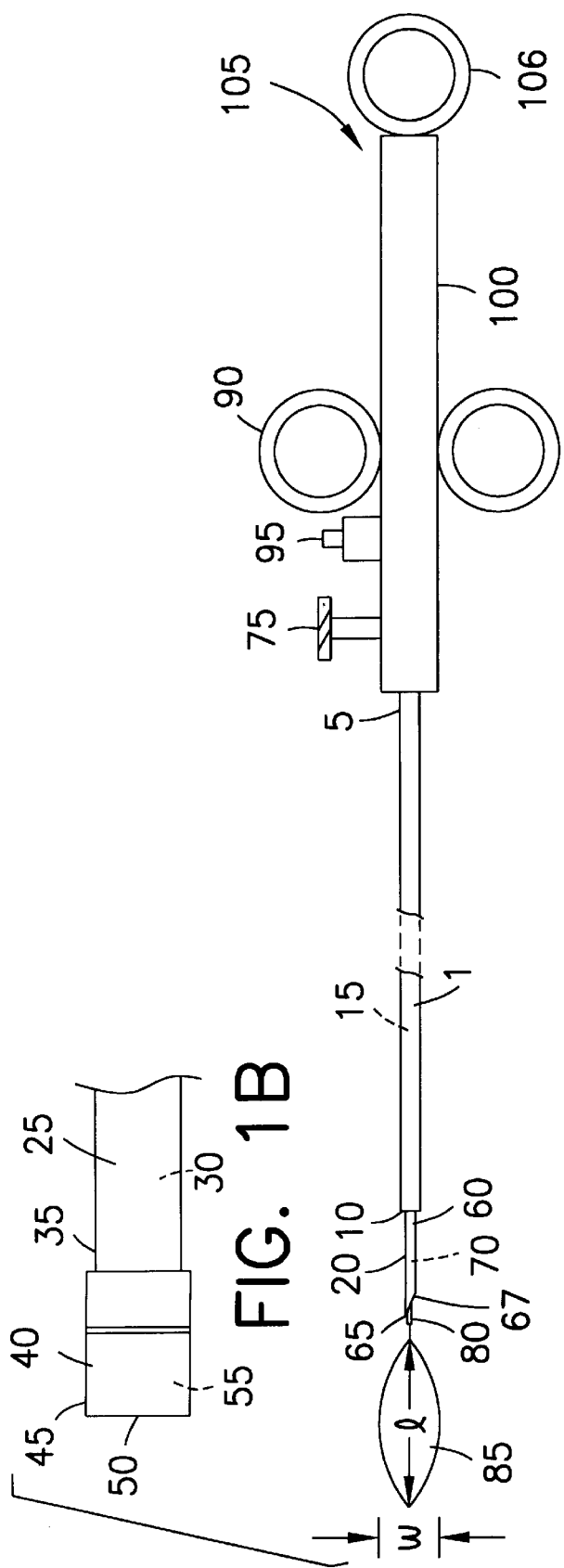
FIG. 1A shows an apparatus according to a first embodiment of the present invention.
FIG. 1B illustrates an aspiration cylinder and a distal end of an endoscope.

As shown in FIG. 1A, an apparatus according to a first embodiment of the invention comprises a sheath 1, having a proximal end 5 and a distal end 10. A lumen 15 extends between the proximal and distal ends 5 and 10, and may preferably have a substantially circular cross-section. A distal aperture 20 is defined at the point where the lumen 15 exits the distal end 10 of the sheath 1.

The sheath 1 is designed to pass through the working channel 30 of an endoscope 25 as can be seen in FIG. 1B. The working channel 30 extends within the endoscope 25 from an accessible end (not shown) to a working end 35 of the endoscope 25. The working channel 30 is sized to allow the free passage of instruments therethrough from an opening formed in the accessible end into the working channel 30 to the working end 35. Of course those skilled in the art will understand that different scopes have working channels 30 of various diameters and that it is necessary only to size the sheath 1 so that a sufficient clearance is preserved within the channel so that the sheath 1 may freely is pass through the working channel 30. Of course, when the sheath 1 extends outside the endoscope 25, the size of the working channel 30 is not a factor in determining the size of the sheath 1.

To configure the endoscope 35 for use with the apparatus according to the invention, aspiration cylinder 40 is coupled to the working end 35 of the endoscope 25. The aspiration cylinder 40, which may preferably be constructed of a transparent bio-compatible plastic such as, for example, polycarbonate or lexan, includes a distal end 45, which defines a distal aperture 50 and an aspirating chamber 55. The aspirating chamber 55 is in communication with the working channel 30 of the endoscope 25 so that an instrument, such as that according to the first embodiment of the present invention, may be passed through the working channel 30, through the aspirating chamber 55, and through the distal aperture 50 of the aspiration cylinder 40.

Endoscope 25 is preferably a single-channel endoscope. Alternately, the surgeon may use a multiple-channel endoscope and use one or more of the other working channels for advancing an instrument, such as a forceps 200 (shown in FIG. 7), basket, needle, or other device, through the endoscope 25, or for accommodating a fiber optical system (not shown). The length of the endoscope 25 should be sufficient to allow the surgeon to use the endoscope 25 and the attached aspiration cylinder 40 to reach the targeted lesions within the patient's body.

An injection needle 60 is disposed through the lumen 15 of the sheath 1. The injection needle 60 defines a lumen 70, which terminates in a distal aperture 67, and has a proximal end (not shown) and a distal tip 65. The cross-sections of the injection needle 60 and the lumen 70 are preferably generally circular, and the cross-sectional diameter of the injection needle 60 is less than the diameter of the lumen 15 of the sheath 1, through which the injection needle 60 passes. As the cross-sectional diameter of the injection needle 60 is less than the diameter of the lumen 15 of the sheath 1, the injection needle 60 is free to move longitudinally through the lumen 15.

Figure 4:
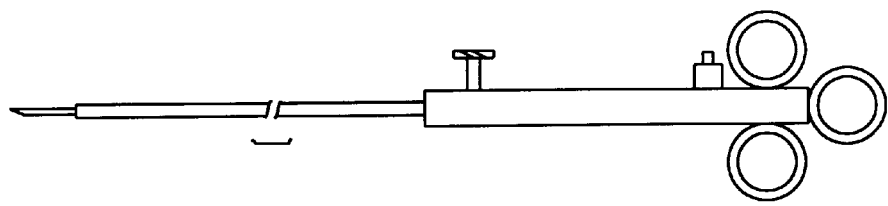
FIG. 4 shows the apparatus according to the first embodiment with the needle handle fully-deployed and the snare handle fully-retracted.

The proximal end of the injection needle 60 is connected to an injection needle handle 75, which slidably engages a handle body 100. The injection needle handle 75, which includes an injection port 77, may be moved longitudinally along the handle body 100 from a fully-deployed position (shown in FIG. 4), wherein the injection needle handle 75 has been moved away from the distal end 105 (formed as a thumb handle 106) of the handle body 100, to a fully-retracted position (shown in FIG. 6), wherein the injection needle handle 75 has been moved proximate to the distal end 105 of the handle body 100 relative to the fully-deployed position. However, if the snare handle 90 is moved further proximally, the needle handle 75 may also be moved further proximally to further retract the needle 75. In the preferred embodiment of the invention, it is also contemplated that the injection needle handle 75 may be positioned in any number of positions between the fully-deployed and fully-retracted positions.

Figure 2:
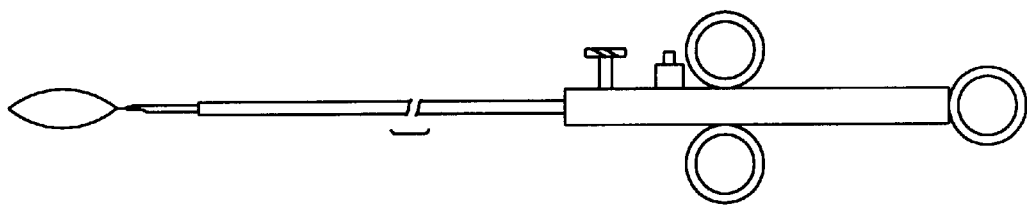
FIG. 2 shows the apparatus according to the first embodiment with both a needle handle and a snare handle fully-deployed.
Figure 3:
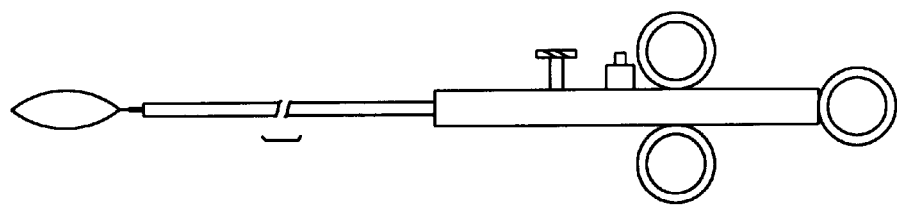
FIG. 3 shows the apparatus according to the first embodiment with both the needle handle and the snare handle partially-deployed.
Figure 5:
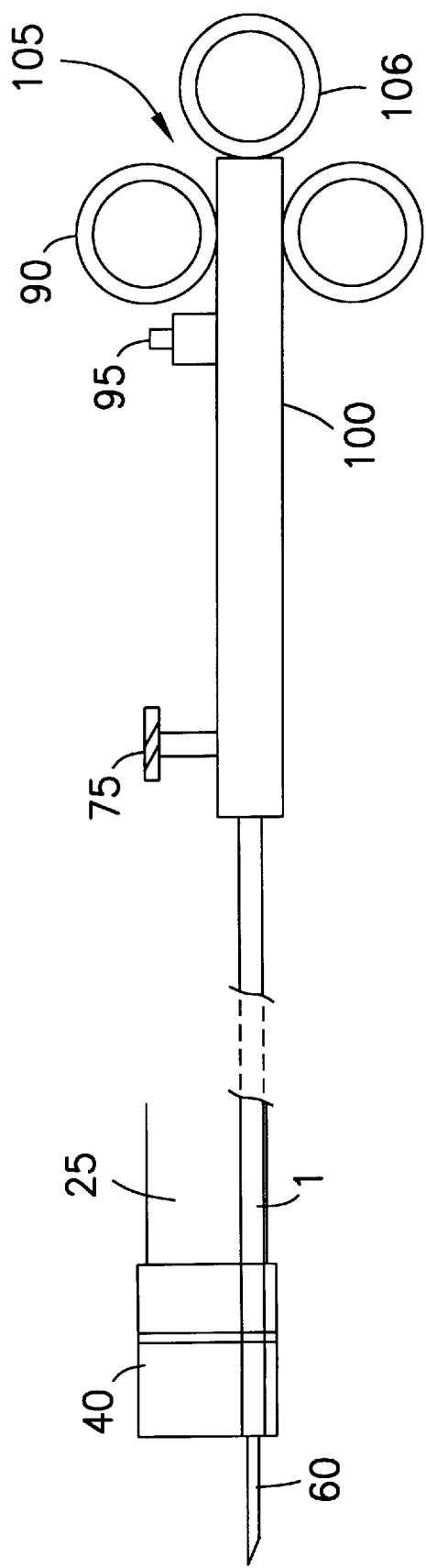
FIG. 5 shows the apparatus according to the first embodiment, arranged as seen in FIG. 4, passing through an endoscope to which an aspiration cylinder has been coupled.
Figure 6:
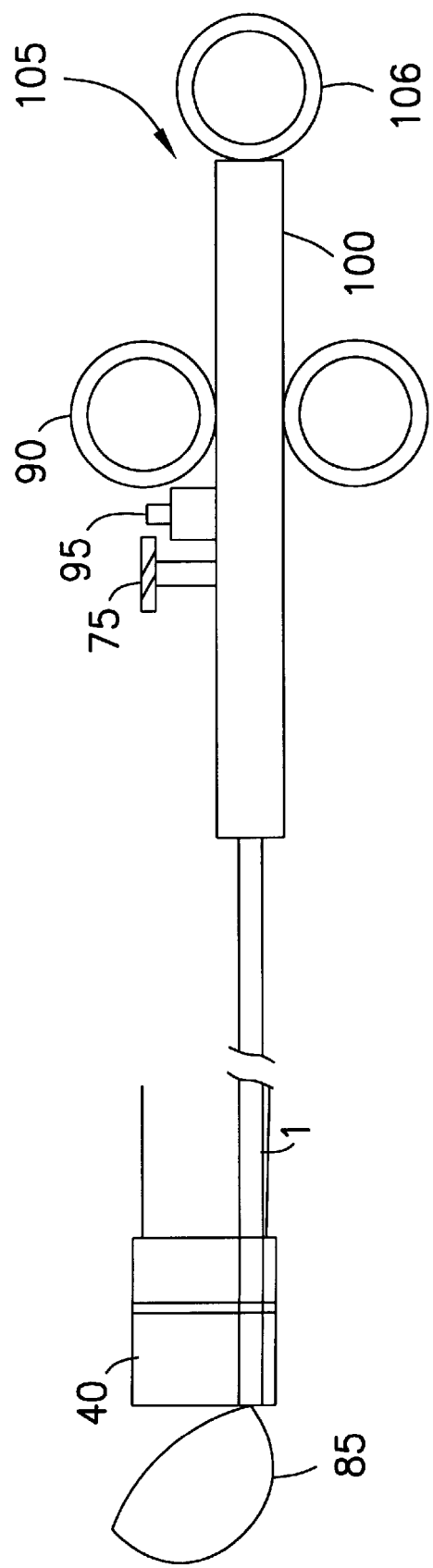
FIG. 6 shows the apparatus according to the first embodiment, arranged as seen in FIG. 5, with the needle retracted and the snare extended and pressing against a lesion.
Figure 7:
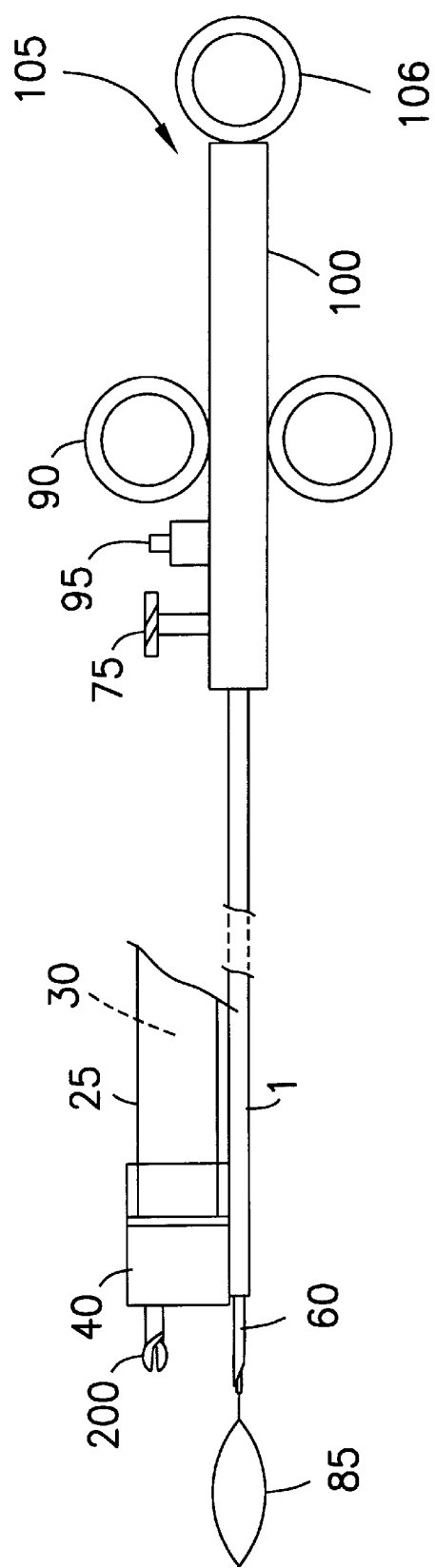
FIG. 7 shows an apparatus according to a second embodiment of the invention, wherein the needle and the snare are located external to the working channel of the endoscope, and the sheath is attached to the aspiration cylinder.
Figure 9:
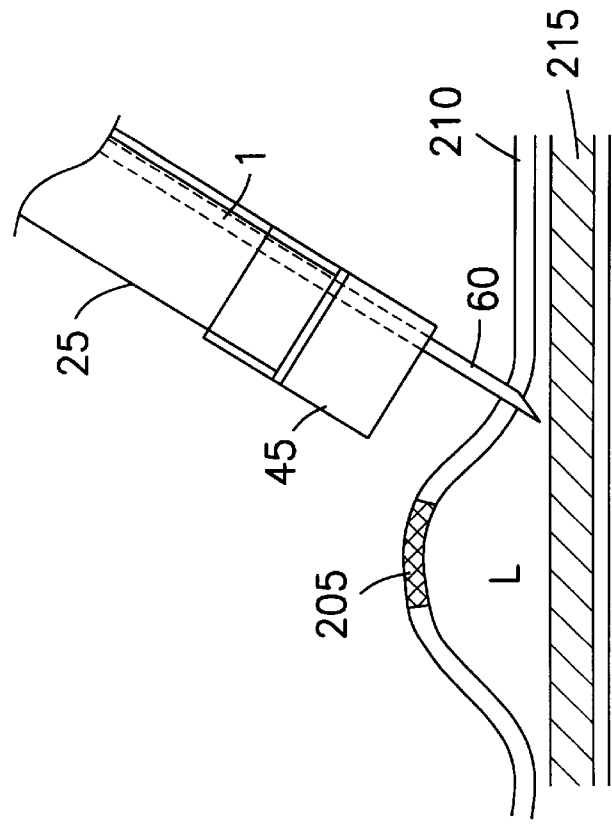
FIG. 9 shows the apparatus according to the first embodiment with the needle injecting a sclerotherapy agent between the mucosa and the muscularis propria.

Movement of the injection needle handle 75 controls and limits the movement of the injection needle 60 through the lumen 15 of the sheath 1. When the injection needle handle 75 is in the fully-deployed position, the distal tip 65 of the injection needle 60 extends through and beyond the distal aperture 20 of the sheath 1 (as seen in FIGS. 2 and 3). When the present invention is used with an endoscope 25 and a aspiration cylinder 40, the distal tip 65 of the injection needle 60 will extend beyond the distal aperture 50 of the aspiration cylinder 40 when the injection needle handle 75 is in the fully-deployed position and the sheath 1 is properly positioned, either within the endoscope 25 (as seen in FIG. 5) or outside the endoscope 25 (as seen in FIG. 7), for carrying out the desired procedure. When the injection needle handle 75 is in a mid-range (as seen in FIG. 3) or a fully-retracted position (as seen in FIG. 6), the distal tip 65 of the injection needle 60 is completely withdrawn within the lumen 15 of the sheath 1. By completely retracting the injection needle 60 within the sheath 1 when the injection needle 60 is not in use, a surgeon can substantially reduce the risk of accidental perforation or entanglement.

An electrosurgical severing snare 80 is disposed within the lumen 70 of the injection needle 60. The severing snare 80 has a proximal end (not shown) and a distal loop 85, which is flexible and made of light-gauge wire such as nitinol or stainless steel. The severing snare 80 is preferably not surrounded by any insulating material so that, when r/f energy is supplied to the severing snare 80, the injection needle 60 is also "hot." However, the sheath 1 is preferably formed as an insulator to guard against short circuiting with an interior surface of the working channel 30 and to protect tissue surrounding the lesion from damage prior to locating a final position and deploying a desired one of the needle 60 and the snare 80. Thus, the needle 60 may be used to cauterize bleeding vessels, or may serve as a point electrical surgery knife.

The diameter of the severing snare 80, the cross-section of which is preferably generally circular, is less than the diameter of the lumen 70 of the injection needle 60, through which the severing snare 80 passes. Those skilled in the art will understand that, because two strands of the wire of the distal loop 85 or the severing snare 80 are received within the distal end of the lumen 70, it is preferable to select a light-gauge wire which is less than half the diameter of the lumen 70. As the cross-sectional diameter of the severing snare 80 is less than the diameter of the lumen 70, the severing snare 80 is free to move longitudinally through the lumen 70. The proximal end of the severing snare 80 is connected to a snare handle 90, which slidably engages the handle body 100, and is in electrical communication with an R/F snare plug 95. Snare handle 90 may be moved longitudinally along the handle body 100 between a fully-deployed position, (shown in FIGS. 2 and 3) in which the distal loop 85 extends from the distal end of the lumen 70, wherein the snare handle 90 is close to the distal end 105 of the handle body 100, and a fully-retracted position (shown in FIG. 4), in which the distal loop 85 is completely retracted into the lumen 70, wherein the snare handle 90 is located adjacent to the thumb ring 106 of the handle body 100. In the preferred embodiment of the invention, it is also contemplated that the snare handle 90 may be positioned in any number of positions between the fully-deployed and fully-retracted positions.

Movement of the snare handle 90 controls and limits the movement of the severing snare 80 through the lumen 70 of the injection needle 60. When the snare handle 90 is in the fully-deployed position, the distal loop 85 of the severing snare 80 extends through and beyond the distal aperture 67 of the injection needle 60. When the present invention is used with an endoscope 25 and a aspiration cylinder 40, the distal loop 85 of the severing snare 80 will extend beyond the distal aperture 50 of the aspiration cylinder 40 when the snare handle 90 is in the fully-deployed position, and the injection needle 60 and sheath 1 are properly positioned, either within the endoscope 25 (as seen in FIG. 6) or outside the endoscope 25 (as seen in FIG. 6), for carrying out the desired procedure.

When the snare handle 90 is in the fully-retracted position, the distal loop 85 of the severing snare 80 is completely withdrawn and collapsed within the lumen 70 of the injection needle 60. Of course, the loop 85 will initially be compressed when it is drawn into the sheath 1 and, by drawing the needle 60 proximally along with the snare loop 85, a user can ensure that the snare loop 85 is collapsed by the sheath 1 before being retracted into the lumen 70. By completely retracting the distal loop 85 and the severing snare 80 within the lumen 70, a surgeon can substantially reduce the risk of accidentally having another instrument, such as a forceps 200 (shown in FIG. 7) become entangled in the distal loop 85. The distal loop 85 of the severing snare 80 is also protected from being accidentally perforated by the injection needle 60 by the fact that the distal loop 85 is located distal to the injection needle 60.

Figure 11:
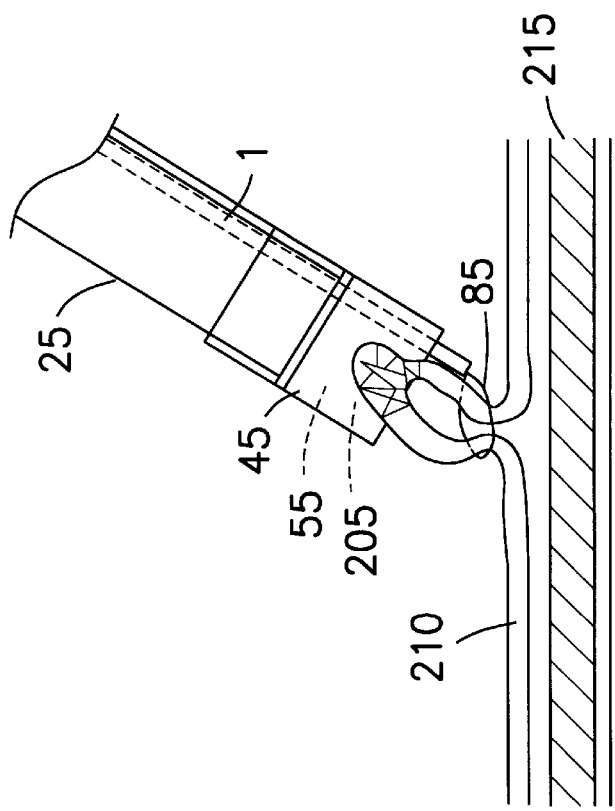
FIG. 11 shows the apparatus according to the first embodiment with the snare being pulled tightly around the targeted lesion.
Figure 10:
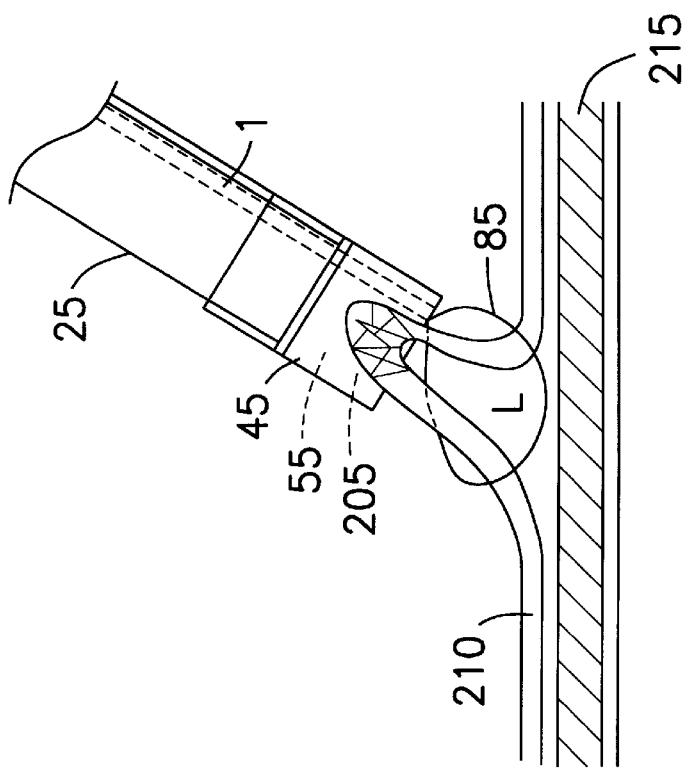
FIG. 10 shows the apparatus according to the first embodiment with the snare being maneuvered over the targeted lesion while the lesion and the surrounding mucosa are aspirated through the inner diameter of the snare into the aspiration cylinder.

For each of the above-described embodiments, when fully-extended and not deformed by another object, the distal loop 85 defines a generally elliptical area, which can be referred to as having a length l and a width w. When the distal loop 85 is retracted into the lumen 70 of the injection needle 60 (i.e., "collapsed"), width w is reduced to approximately the diameter of the lumen 70. Accordingly, the area defined by the distal loop 85 is substantially smaller after the distal loop 85 has been collapsed than before it has been collapsed. Distal loop 85 is able to be collapsed upon being retracted because the wire that comprises the distal loop 85 is flexible. The distal loop 85 is preferably biased so that, when the distal loop 85 is redeployed it will return to its precollapsed state and define roughly the same area as it did before it was collapsed within the lumen 70. In addition as shown in FIGS. 11 and 12, the snare loop 85 may be biased so that, when outside the lumen 70, the loop 85 extends in a plane disposed at an angle, e.g., 90°, relative to the longitudinal axis of the needle 60. That is, the loop 85 may be biased so that, when deployed, it extends across an opening of the aspiration cylinder 40. This facilitates placement of the loop 85 over a lesion aspirated into the aspiration cylinder 40.

The R/F snare plug 95 is provided to transmit energy from an external source (not shown) to the distal loop 85 of the severing snare 80.

In the preferred embodiment of the invention, the sheath 1 is designed to pass through the working channel 30 of the endoscope 25. By using the device in this manner, the overall cross-sectional area of the endoscope is not increased due to the presence of the sheath 1, injection needle 60, and severing snare 85, although the aspiration cylinder 40 may slightly increase the profile of the endoscope 25. Furthermore, because the severing snare 80 is coaxial with the injection needle 60, the combination of the two instruments takes up approximately the same amount of room within the working channel 30 that a standard injection needle would.

If, however, the injection needle 60 and the severing snare 80 were positioned side-by-side and electrically isolated from one another by separate sheaths, the combination of the two instruments would require more room within the working channel 30, thereby necessitating the use by the surgeon of a large endoscope or the elimination of the advantages of having both instruments simultaneously present at the site of the lesion and, instead, having to perform several "exchanges" as discussed in the prior art.

Thus, a surgeon using the present device may use an endoscope with a relatively small working channel 30 while still enjoying the benefits of locating both an injection needle 60 and a severing snare 80 simultaneously at the site of a lesion. Alternately, the surgeon may use any "free space" within an larger diameter endoscope (such as the diameter that would be needed if the two instruments were positioned side-by-side) for passing other instruments, such as a forceps 200, through the working channel 30. Also, the surgeon could select an injection needle 60 and a severing snare 80 having slightly larger diameters, thereby allowing for more injection flow through the injection needle 60 and for a stronger severing snare 80.

In an alternate embodiment as shown in FIG. 7, the sheath 1 may be located external to the working channel 30 of a relatively small diameter endoscope 25. In such a configuration, a portion of the sheath 1 is attached to the aspiration cylinder 40 by tape, cable ties, or mesh means (not shown). While this configuration enlarges the overall profile of the endoscope 25 and aspiration cylinder 40 assembly, the surgeon is then free to use another instrument, such as a forceps 200, basket, needle, or cautery device, through the working channel 30 of the endoscope 25, without having to first remove the injection needle 60 and the severing snare 80 from the patient. The open working channel 30 of the endoscope 25 also allows for multiple combinations of instruments to be used within the working channel 30 without having to remove the endoscope 25 from the body of the patient.

A novel method for ligating a lesion will now be described with reference to FIGS. 8–13.

First, a surgeon administers a local pharyngeal anesthesia or general anesthesia to the patient and introduces into the patient an endoscope 25 having an aspiration cylinder 40 coupled thereto. The surgeon then passes the sheath 1 through the working channel 30 of the endoscope 25 with the sheath 1 protecting the endoscope from being scraped or damaged by the needle as it is passed through the working channel 30. A needle 60 is passed through the lumen 15 of the sheath 1 with a severing snare 80 disposed within the lumen 70 of the needle 60. Alternately, the surgeon may forgo use of a aspiration cylinder 40 and may attach the sheath 1 to the outside of the endoscope 25.

Figure 8:
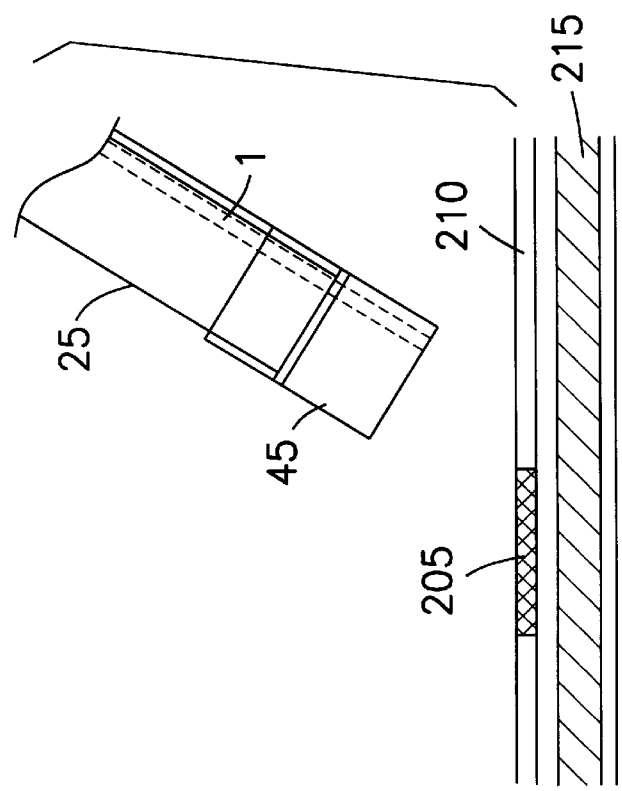
FIG. 8 shows the apparatus according to the first embodiment located adjacent to a targeted lesion.

As shown in FIG. 8, the surgeon positions the distal end of the aspiration cylinder 40 adjacent to the lesion 205 that the surgeon wishes to remove. The lesion 205 as shown in FIGS. 8–13 is illustrative of a lesion found in the gastrointestinal tract and may, for example, be associated with early gastric cancer or adenoma. The lesion 205 is part of the mucosa 210, and is positioned over a submucosa layer 215 (the muscularis propria).

Next, the surgeon passes an injection needle 60 (shown in FIG. 9) through the mucosa 210, and injects a sclerotherapy agent L or saline solution between the mucosa 210 and the muscularis propria 215, thereby separating the mucosa 210 from the muscularis propria 215. It is preferable that a sclerotherapy agent L, such as Glyceol™, be used rather than saline solution because the bulge formed between the mucosa 210 and muscularis propria 215 lasts longer when a sclerotherapy agent is used.

Once the lesion 205 has been elevated on a bed of sclerotherapy agent L, the surgeon deploys the snare 80 and positions the loop 85 around the lesion 205 and then aspirates the lesion 205 through the loop 85 into the aspirating chamber 55 of the aspiration cylinder 40 (shown in FIG. 10) and tightens the loop 85 around the tissue to sever the lesion 205 (shown in FIG. 12).

If the surgeon is using an electrosurgical severing snare, as described in the background of the invention, he would apply the appropriate R/F energy (i.e., "cutting," "coagulating," or "blended") to the snare through an R/F snare plug 95 while severing the lesion 205. As shown in FIG. 13, after the lesion 205 has been severed, it may be retained in the aspiration cylinder 40 to be removed from the body for further pathology study or aspirated out of the aspirating chamber 55 to pass through the body. If the lesion 205 is aspirated out of the aspiration cylinder 40, the surgeon may immediately proceed to treat a subsequent lesion (not shown) without having to remove the endoscope 25 and the aspiration cylinder 40 from the body.

Alternately, the surgeon may pass an instrument, such as a forceps 200, through the working channel 30 or an external or an addition lumen (not shown) of the endoscope 25 to grasp and retrieve the lesion 205. If the sheath 1 occupies the working channel 30 and no other lumen is provided, then the surgeon could exchange sheath 1 for the desired instrument 200, or attempt to pass the instrument 200 around the sheath 1 within the working channel 30. This exchange would be eliminated, however, if the sheath 1 were connected to the outside of the aspiration cylinder 40 (as seen in FIG. 7), thereby freeing up the working channel 30 of the endoscope 25 for other instruments, such as the forceps 200.

In addition, if the surgeon opts not to perform EAM and instead elects for SAP, the forceps 200, rather than suction, would be used to separate the lesion 205 and the mucosa 210 from the muscularis propria 215. Accordingly, it would be desirable to adapt the present invention to allow for both the coaxial needle 60/severing snare 80 instrument and the forceps 200 to be simultaneously located at the site of the lesion 205. In accordance with an alternate embodiment of the present invention, the sheath 1 could be located external to the endoscope 25, thereby still allowing the surgeon to use a single-channel (rather than a double-channel) endoscope 25 to perform the SAP procedure.

Figure 14:
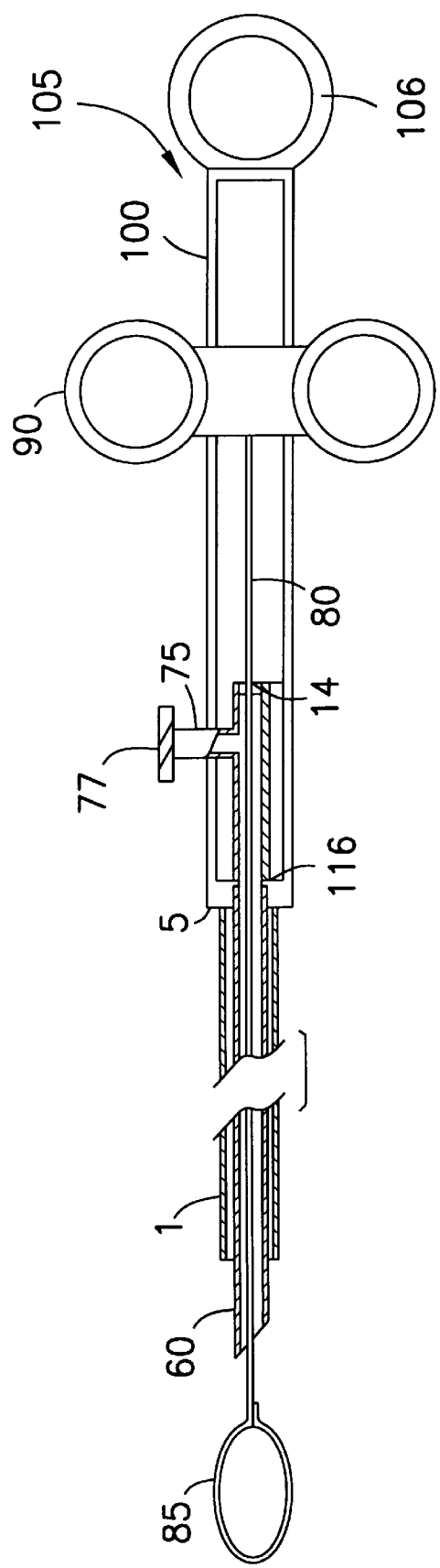
FIG. 14 shows a cross section of the apparatus of FIG. 1.
Figure 15:
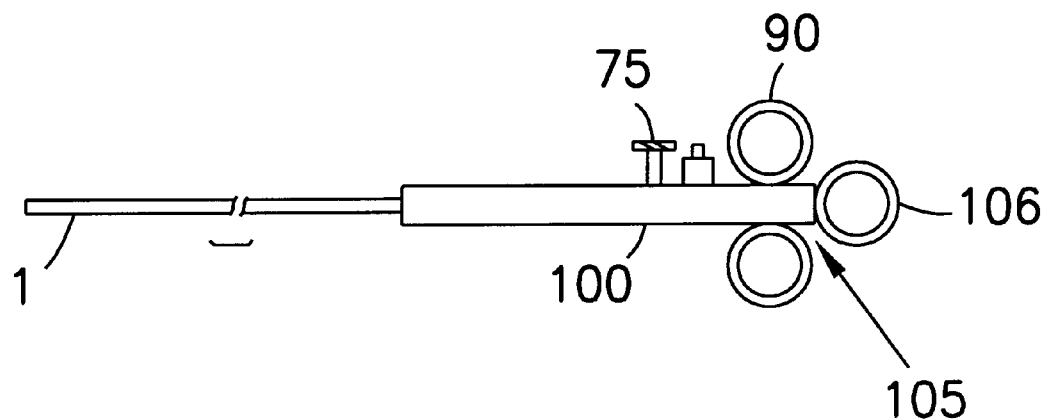
FIG. 15 shows the apparatus of FIG. 1A with the needle and the snare in fully retracted positions.

Those skilled in the art will understand that the injection needle handle 75 is preferably coupled to the severing snare handle 90 so that, when the severing snare 80 is retracted, the injection needle 60 is also retracted at least until the distal tip 65 of the injection needle 60 is received within the sheath 1. For example, after grasping tissue, the diameter of the distal loop 85 will be expanded to surround the tissue and, when the snare 80 is retracted while the injection needle 60 is fully or partially deployed, the expanded loop 85 will be too large to enter the injection needle 60. Thus, the needle 60 will be pushed proximally by the proximal travel of the distal loop 85 until the severing loop 85 comes into contact with the distal end 10 of the sheath 1. As shown in FIG. 14, as the snare 80 is drawn further into the sheath 1, decreasing the diameter of the distal loop 85, there is no impediment to the proximal travel of the needle 60 which is pushed further proximally into the housing 100. FIG. 15 shows the apparatus of FIG. 14 in which no stop 110 is provided to limit the proximal travel of the needle 60, wherein both the snare 80 and the needle 60 are completely withdrawn into the sheath 1.

Figure 16:
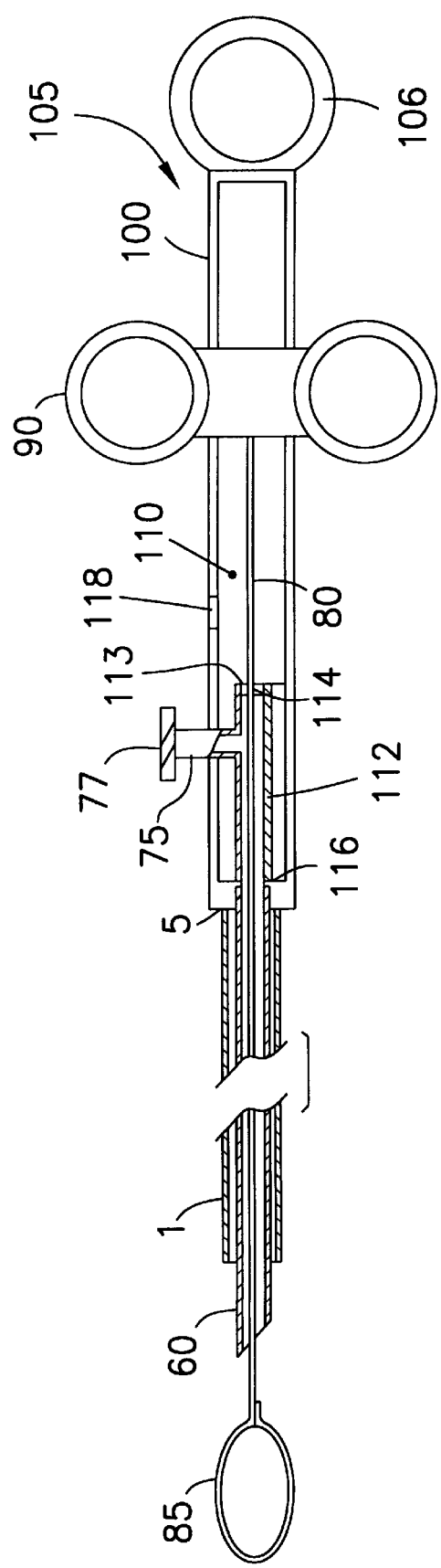
FIG. 16 shows a cross-section of an additional embodiment of the invention including a stop for limiting the movement of the snare and needle.

FIG. 16 shows a further embodiment of the apparatus according to the present invention in which a mechanism is provided to control the motion of the needle 60 and the snare 80. Specifically, the apparatus of FIG. 16 includes a stop 110 formed as a rod extending across the interior lumen of the handle body 100 preferably substantially perpendicular to a longitudinal axis of the handle body 100. The stop 110 contacts the snare handle 90 to define the distal-most position of the snare handle 90 and, consequently, the distal-most position of the snare 80. Similarly, the stop 110 contacts the needle handle 75 to define the proximal-most position of the needle handle 75 and, consequently, of the needle 60. Those skilled in the art will understand that the rod 110 may be formed as a separate piece bonded to, or molded into, the interior of the handle body 100. In addition, an increased diameter portion 112 of the needle 60 is provided to further define the proximal and distal limits of travel of the needle 60. Specifically, the proximal end 114 of the increased diameter portion 112, which is formed as a seal to seal the interior lumen 70 of the needle 60, facilitates contact between the stop 110 and the needle 60 and includes a receiving cavity 113 to ensure that the needle 60 does not travel proximally past the stop 110. A distal end 116 of the increased diameter portion 112 abuts a shoulder formed on a distal end of the handle body 100 when the needle 60 is in a distal-most position. In addition, when the needle actuator 75 is retracted to the proximal-most position, it can be rotated about the longitudinal axis of the housing 100 so that the needle actuator 75 is locked into a locking bay 118.

Figure 17:
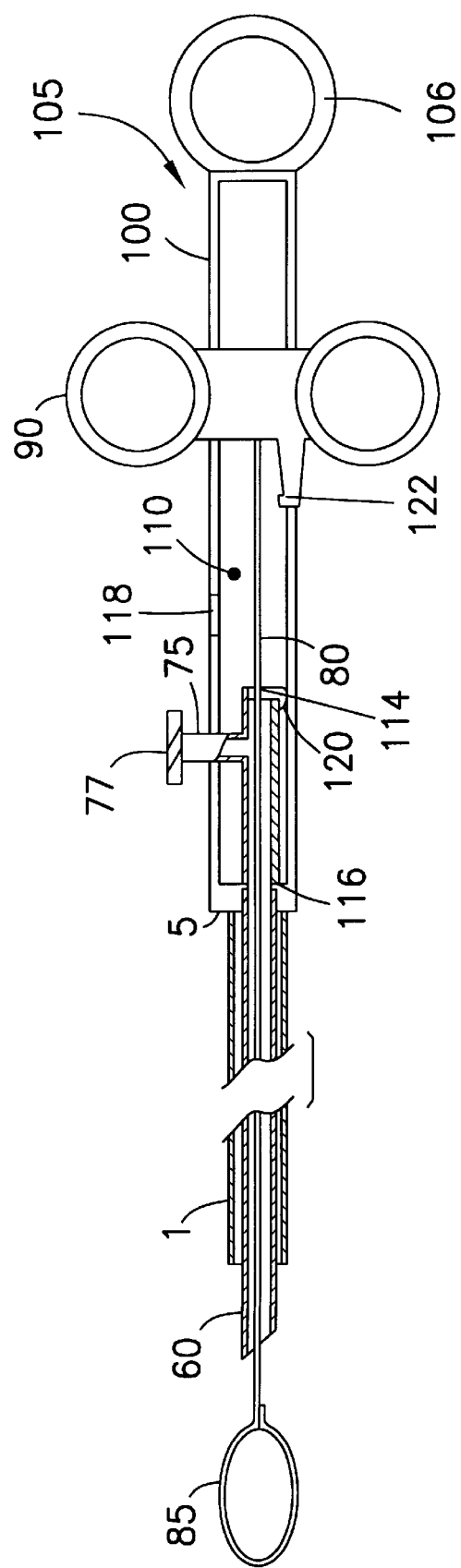
FIG. 17 shows a cross-section of a further embodiment including a mechanism for latching the snare and needle together so that they may be retracted in unison.

FIG. 17 shows a device similar to that of FIG. 16 except that the increased diameter portion 112 of the needle 60 includes a detente 120 extending from the proximal end 114. This detente 120 cooperates with a latch 122 formed on a portion of the snare handle 90 extending within the housing 100 so that as the snare 80 is pushed distally, the latch 122 will abut the proximal end 114 of the increased diameter portion 112 pushing the needle 60 out to the fully deployed position. of course, the needle 60 may be independently deployed by moving the needle handle 75 distally. In any case, when the needle 60 reaches the fully deployed position and the distal end 116 abuts the shoulder formed on the distal end of the handle body 100, the latch 122 moves underneath the detente 120 and locks the snare handle 90 to the needle 60. Thus, when the snare 80 is withdrawn proximally, the needle 60 is also drawn back into the sheath 1 until further proximal travel of the needle 60 is stopped by contact between the distal end 114 and the stop 110 at which point the latch 122 is released from the detente 114 and the snare 80 is retracted into the interior lumen 70 of the needle 60.

Still other objects and advantages of the present invention will become readily apparent to those skilled in this art from the above-recited detailed description, wherein the preferred embodiment of the invention has been shown and described.

The description of the preferred embodiment is simply by way of illustration of the best mode contemplated for carrying out the invention. As will be realized, the invention is capable of other and different embodiments, and its several details are capable of modification in various respects, all without departing from the invention. Accordingly, the drawings and descriptions are to be regarded as illustrative in nature, and not as restrictive.

What we claim is:

1. A lesion treating system comprising:

an endoscope defining a working channel extending therethrough;

a sheath disposed within the working channel of the endoscope so that a distal end of the sheath is located adjacent to a distal end of the working channel;

a fluid injection needle having a tissue piercing tip at a distal end thereof and a fluid injection port at a proximal end thereof, the fluid injection needle extending through the sheath, the fluid injection needle defining a central lumen which extends from the fluid injection port to the tissue piercing tip; and a snare extending through the central lumen, the snare having a loop formed at a distal end thereof.

2. The system according to claim 1, further comprising an aspiration housing connected to a distal end of the endoscope.

3. The system according to claim 2, wherein the sheath extends into the aspiration housing and wherein the fluid injection needle and the snare may be extended into and retracted from the aspiration housing.

4. The system according to claim 1, wherein the snare comprises an electrically conductive material and wherein a proximal end of the snare is coupled to a contact for coupling the snare to a source of R/F energy.

5. A method for severing a portion of tissue comprising the steps of:

inserting into a body an endoscope defining a working channel extending therethrough, wherein a sheath is disposed within the working channel of the endoscope so that a distal end of the sheath is located adjacent to a distal end of the working channel and wherein a fluid injection needle, having a tissue piercing tip at a distal end thereof and having a fluid injection port at a proximal end thereof and which defines a central lumen which extends from the fluid injection port to the tissue piercing tip, extends through the sheath and further wherein a snare having a loop formed at a distal end thereof extends through the central lumen;

positioning the endoscope adjacent to a portion of tissue to be severed; and performing one of the steps of:

extending the fluid injection needle from a distal end of the endoscope to penetrate the tissue to be severed to inject fluid into the tissue; and extending the snare from the distal end of the endoscope to encircle and sever the tissue to be severed.

6. The method according to claim 5, wherein the step of extending the fluid injection needle from the distal end of the endoscope to penetrate the tissue to be severed to inject fluid into the tissue is performed and then the step of extending the snare from the distal end of the endoscope to encircle and sever the tissue is performed.

7. The method according to claim 5, further comprising the step of drawing the portion of tissue to be severed into a chamber formed at the distal end of the endoscope, wherein the drawing step is performed after the step of extending the fluid injection needle from the distal end of the endoscope to penetrate the tissue to be severed to inject fluid into the tissue.

8. The method according to claim 5, further comprising the step of drawing the portion of tissue to be severed into a chamber formed at the distal end of the endoscope, wherein the drawing step is performed prior to the step of extending the snare from the distal end of the endoscope to encircle and sever the tissue to be severed.

9. The method according to claim 5, wherein the fluid injected into the tissue is a sclerotherapy agent.

10. The system according to claim 1, further comprising:

a needle actuator for moving the fluid injection between a retracted position in which the tissue piercing tip is received within the sheath and an injection position in which the tisue piercing tip extends distally beyond the distal end of the sheathl and a snare actuator for moving the snare between a covered position in which the loop is received within the central lumen and an extended position in which the loop extends distally from the central lumen beyond the tissue piercing tip.

11. The system according to claim 10, wherein the needle actuator is coupled to the snare actuator so that, as the snare actuator is moved from the extended position to the covered position while the needle is in the injection position, the needle is moved from the injection position to the retracted position.

12. The system according to claim 10, further comprising a handle coupled to a proximal end of the sheath, wherein the snare actuator and the needle actuator are coupled to the handle.

13. The system according to claim 12, wherein the handle includes a snare locking mechanism for locking the snare actuator in a desired position wherein the desired position may be one of the covered position, the extended position and any position intermediate between the covered and extended positions.

14. The system according to claim 12, wherein the handle includes a needle locking mechanism for locking the needle actuator in a desired position wherein the desired position may be one of the retracted position, the injection position and any position intermediate between the retracted and injection positions.

\* \* \* \* \*